United States Patent [19]

Sardelis et al.

[11] Patent Number: 5,269,806
[45] Date of Patent: Dec. 14, 1993

[54] I-BEAM NEEDLE HAVING TRUE I-BEAM CROSS-SECTION

[75] Inventors: Timothy A. Sardelis, Somerset; Paul J. Parisi, Mahwah; Lester E. Schaible, Somerville; Lawrence P. Trozzo, Hillsborough; Matthew L. Wolczynski, High Bridge, all of N.J.

[73] Assignee: Ethicon, Inc., Somerville, N.J.

[21] Appl. No.: 959,198

[22] Filed: Oct. 9, 1992

[51] Int. Cl.$^5$ .............................................. A61B 17/00
[52] U.S. Cl. .................................... 606/222; 606/223
[58] Field of Search ................................ 606/222-227

[56] References Cited

U.S. PATENT DOCUMENTS

| | | | |
|---|---|---|---|
| 1,321,011 | 11/1919 | Cottes | 606/223 |
| 1,592,897 | 7/1926 | Morton | 606/223 |
| 1,599,059 | 9/1926 | Morton | 606/223 |
| 2,092,929 | 9/1937 | Ovington | 606/222 |
| 3,160,157 | 12/1964 | Chisman | 606/223 |
| 4,799,484 | 1/1989 | Smith et al. | 606/223 |

*Primary Examiner*—Stephen C. Pellegrino
*Assistant Examiner*—Gary Jackson
*Attorney, Agent, or Firm*—Emil Richard Skula

[57] ABSTRACT

A surgical needle having an I-beam configuration is disclosed. The surgical needle comprises an elongated member having an I-beam cross section wherein two opposed flange members are connected by a web member. The elongated member has a piercing point extending from its distal end. A cylindrical mounting section extends from the proximal end of the needle for receiving an end of a suture. The needle has increased resistance to bending and buckling when compared to conventional needles and does not have an increase in resistance or drag.

21 Claims, 2 Drawing Sheets

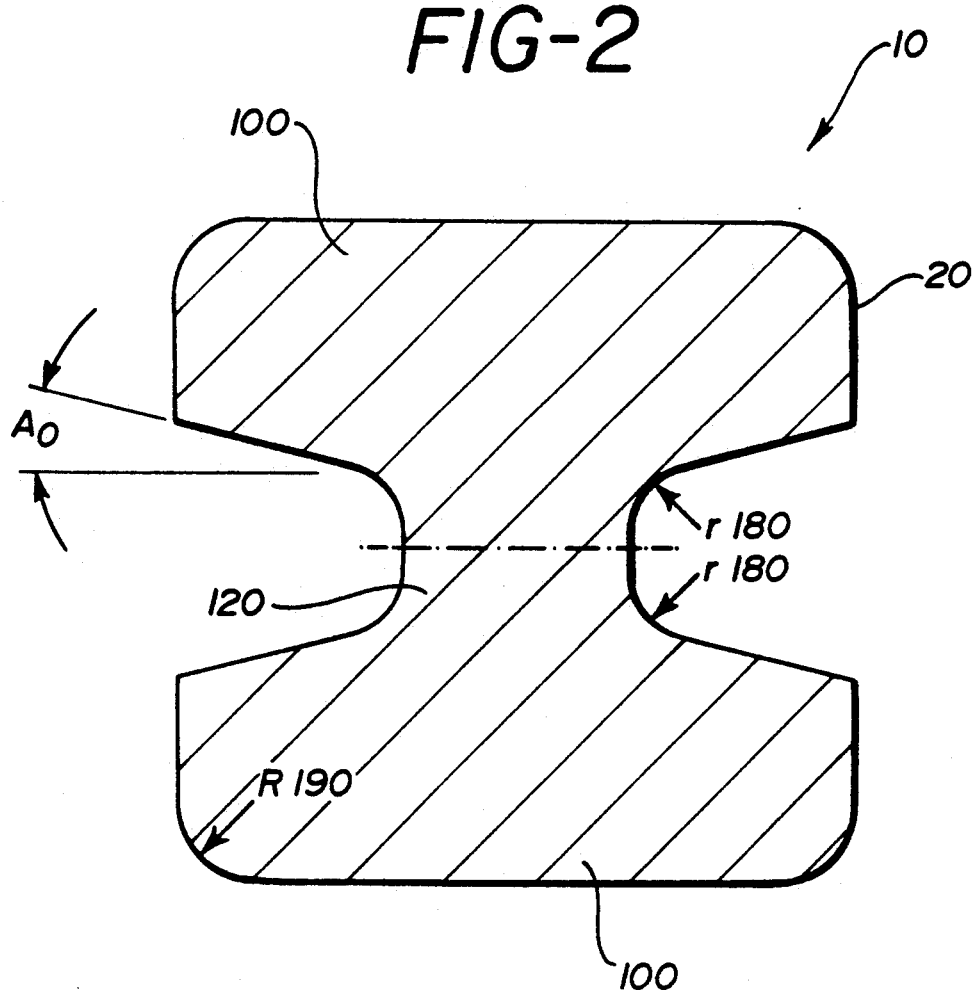

I-BEAM NEEDLE HAVING TRUE I-BEAM CROSS-SECTION

TECHNICAL FIELD

The Field of Art to which this invention relates is surgical needles.

BACKGROUND OF THE INVENTION

Surgical needles have been long known in the medical and surgical arts for use with sutures to join tissue at incisions, tears, cuts, and the like. A conventional surgical needle typically consists of a shaft member having a sharpened distal piercing tip and a proximal end having a cavity for mounting the end of a surgical suture. Surgical needles are known to have various configurations including straight needles and curved needles.

Surgical needles are required to have various performance characteristics. The surgical needles must have good ease of penetration, and, minimal resistance to being pulled through tissue. In addition, it is important for the needle shaft to be resistant to buckling or bending as the surgeon inserts the needle into tissue. Generally speaking, the force required to push a needle through tissue will vary with the particular type of tissue, e.g., skin, muscle, arteries, veins, internal organs, tendons, cartilage, etc. Surgical needles may have blunt tips, piercing tips, cutting tips or combination piercing-/cutting tips.

When using a surgical needle, it is a common practice for the surgeon or physician to grasp the needle with a conventional needle holder. A conventional needle holder typically has a pair of opposed, moveable elongated jaws connected to a pair of handles. The jaws are hinged and moveable with respect to each other and movement is controlled by movement of the handles. When grasping a needle, it is important that the needle not slip within the jaws of the needle holder while the surgeon is attempting to penetrate tissue or pull the needle through tissue. For example, U.S. Pat. No. 4,799,484 discloses a needle having superior ease of penetration with a configuration which provides excellent resistance to slipping and twisting when grasped by a needle holder. The needle disclosed in that patent has a configuration referred to as an "I-beam", however, the cross-section of the needle is actually rectangular.

There is a constant search in this art for needles having improved resistance to bending or buckling while retaining a desirable configuration to reduce the drag on the needle as it is being forced or pushed through tissue.

Therefore, it is an object of the present invention to provide a surgical needle having a true I-beam configuration.

It is a further object of the present invention to provide a surgical needle having a configuration which provides improved resistance to bending and buckling while not increasing the drag force required to pull the needle through tissue.

It is yet a further object of the present invention to provide a surgical needle which is easy to grasp and to hold securely in a conventional needle holder.

SUMMARY OF THE INVENTION

Accordingly, a surgical needle having an I-beam configuration is disclosed. The surgical needle comprises an elongated member with a distal end and a proximal end. A piercing point extends from the distal end, while a cylindrical section, having a cavity therein for receiving a suture, extends from the proximal end. The needle may be curved or straight. The piercing point may optionally have a cutting edge. The cross-section of the elongated member has a true I-beam configuration wherein two opposed, parallel flange members are connected by a perpendicular web member.

Another aspect of the present invention is the combination of a surgical suture and the above-described surgical needle.

Yet another aspect of the present invention is a method of suturing mammalian tissue using the above-described surgical needle wherein at least one needle pathway is formed in the tissue by the needle, and the suture is moved through each needle pathway.

The I-beam configured surgical needles of the present invention have improved resistance to bending and buckling. Surprisingly, the I-beam configured needles do not produce increased drag when pushed or pulled through tissue when compared with needles having conventional cross-sections. In addition, the elongated member section of the needle is easy to grasp with a conventional needle holder. The I-beam configuration resists twisting or turning when engaged in the jaws of a conventional needle holder.

The foregoing and other features and advantages of the present invention will become more apparent from the following description and accompanying drawings.

BRIEF DESCRIPTION OF THE DRAWINGS

FIG. 2 is a cross-sectional view taken along View Line 2—2 of the surgical needle of the present invention.

BEST MODE FOR CARRYING OUT THE INVENTION

Figure 1:
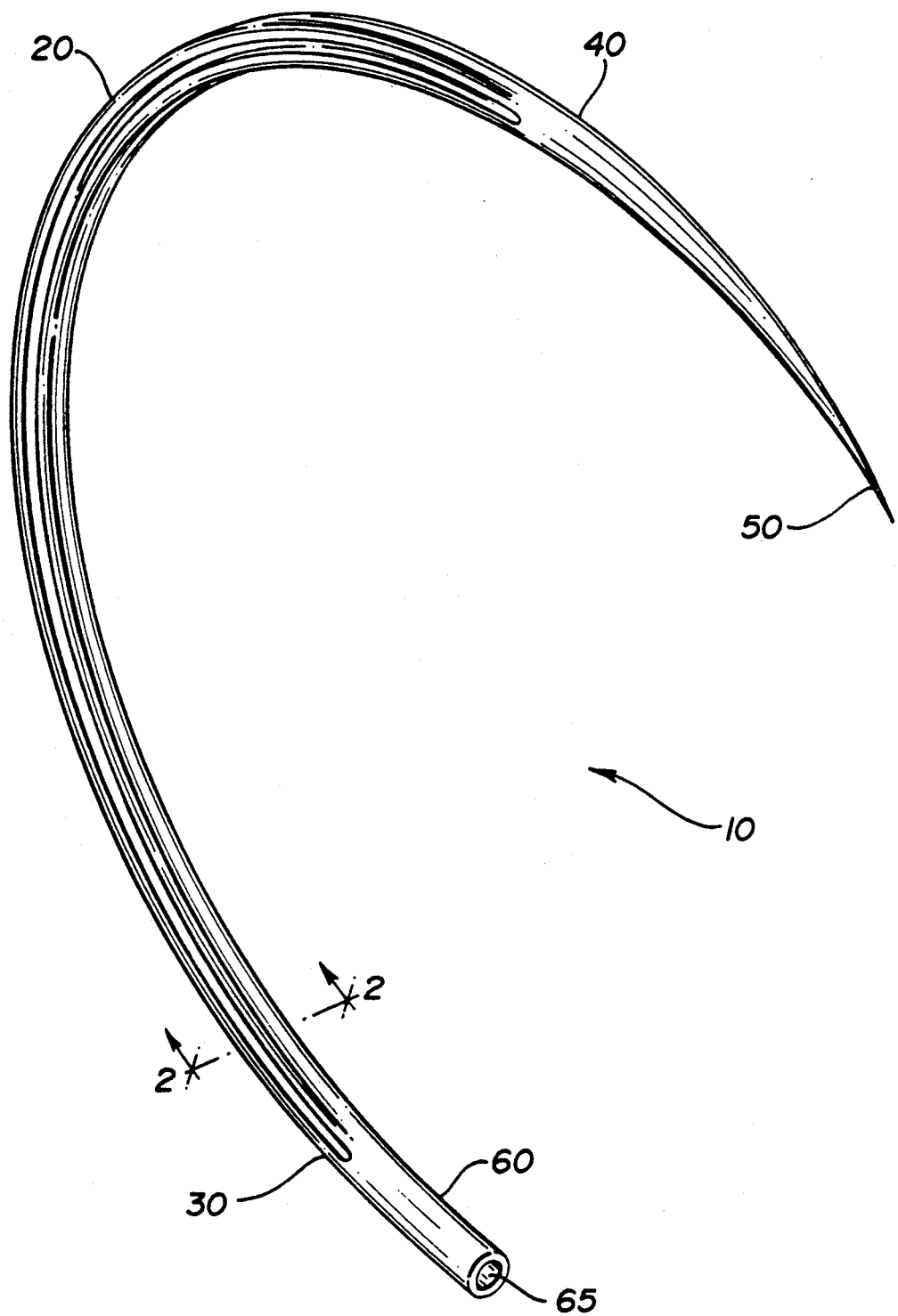
FIG. 1 is a perspective view of a surgical needle of the present invention.

U.S. Pat. No. 4,799,484 is incorporated by reference. Referring to FIG. 1, the surgical needle 10 of the present invention is seen to have a central elongated member 20 having a distal end 40 and a proximal end 30. Extending from the distal end 40 is the piercing point 50. Extending from the proximal end 30 is the cylindrical member section 60 having concentric, internal mounting cavity 65 therein. The needle 10 is shown in a curved configuration in FIG. 1, however, it will be appreciated by those skilled in the art that the needle 10 may have other conventional configurations including a straight configuration or a combination of a straight configuration and a curved configuration.

Referring to FIG. 2, the needle 10 is seen to have a cross-section of a true I-beam. The elongated member 20 is seen to have a pair of opposed, parallel flange members 100 connected by a perpendicular web member 120. Preferably, one or more of the dimensions of member 20 will vary, moving along the member 20, from a maximum dimension to a minimum dimension, as the distal end 40 of needle 10 is approached. However, this variation may not be present or would be significantly attenuated with a cutting edge design. One or more of the dimensions of member 20 may also vary from a maximum dimension to a minimum dimension as the proximal end 30 and the tubular member section 60 are approached.

Referring to FIG. 2, it will be appreciated by those skilled in the art that the dimensions of the web member 100 and the flange members 100, as well as the size of angle $A_o$ and the height of the needle 10 cross-section, will vary according to the type of material utilized to manufacture the needle 10 as well as with the particular tissue application for which the needle is designed. The dimensions of the web member 100 and the flange members 120 and the size of angle $A_o$ and the height of the needle 10 cross-section will be sufficient to provide effective resistance to bending. It is well within the purview of one skilled in the art to select the parameters depending upon the particular application and the material of construction of needle 10. For example, the needles 10 of the present invention may typically have an original diameter of 0.15 mm to about 1.5 mm (i.e., the diameter of the needle prior to forming an I-beam cross-section). The length of the needle may vary from about 6 mm to about 65 mm. The diameter of the needle will vary depending upon the particular application for which the needle is designed. For example, the diameter of the needle 10 may range from 0.15 mm to about 0.5 mm for ophthalmic use and from about 0.15 mm to about 1.5 mm for cardiovascular use. The overall height of the needle cross-section may have a dimension of about 0.14 mm to about 1.4 mm. The overall width of the flange member 120 may typically be about 0.12 mm to about 1.2 mm. The thickness of the flange member may be about 0.05 mm to about 0.5 mm. The thickness of the web member 120 may be about 0.07 mm to about 0.80 mm measured at mid-line. The height of the web member 120 may be about 0.04 mm to about 0.4 mm measured at its maximum. The angle $A_o$ as seen in FIG. 2 can vary from about 0 degrees to almost about 90 degrees. A is defined as the angle of declension between the flange and the web member 120. Radii r 180 and R 190 are included for alleviation of angles.

The needle point 50 may have a variety of conventional point configurations including taper point, taper cut, blunt point, cutting edge and spatulated.

Various types of conventional sutures may be used with the needles 10 of the present invention. The sutures include absorbable sutures, both natural and synthetic, and, non-absorbable sutures, such as silk, steel and polypropylene. The sutures may have diameters ranging from about 11/0 USP ophthalmic to about to 7 USP sternotomy.

The materials used to manufacture the needles 10 of the present invention include austenitic, martensitic or precipitation hardening stainless steels, or nickel-plated carbon steel. It is particularly preferred to use a conventional stainless steel such as Types AISI 302, 420, and 455.

The needles 10 of the present invention are manufactured using conventional needle manufacturing techniques in the following manner. Starting with round wire, the wire is straightened and cut into needle blanks. Then, the point 50 is ground or pressed or formed into the distal end 40 using conventional techniques and equipment. The elongated member 20 is then shaped to the desired configuration. The needle 10 is given an I-beam configuration by processing the needle blanks in a conventional mechanical press having dies which form the I-beam configuration into the sides, top and bottom of the needle 10 while holding the needle blank immobile. A hole is drilled or a channel is pressed into the tubular member 60 to form mounting cavity 65. The needle is then curved if a curved configuration is desired. If necessary the needle is then heat treated and electropolished.

The needles 10 of the present invention may be used to suture tissue in the following conventional procedures including, but not limited to, general wound closure, endoscopic surgery, plastic surgery, microsurgery, cardiovascular, and ophthalmic surgery and equivalents thereof.

The needles 10 are used in a conventional manner. The appropriate size, shape, and needle tip, must produce a controlled hole in tissue to allow passage of the attached suture. The needle 10 is typically grasped along elongated member 20 with a conventional needle grasper. The point 50 is pushed through tissue until the point 50 is seen to emerge. The needle is then released and re-grasped to pull the needle 10 and attached suture through the tissue. The procedure is repeated as required to suture or close the wound or incision.

The principles and practice of the present invention are illustrated by the following example although not limited thereto.

EXAMPLE 1

A surgical needle 10 of the present invention, as illustrated in FIG. 1, was fabricated from Type 455 stainless steel alloy. The needle 10 had a conventionally curved configuration. The needle 10 had an original diameter of 0.46 mm before fabrication of the I beam cross-section. In the final I-beam configuration the overall height of the I beam cross-section is about 0.51 mm. The overall width of the I beam is about 0.41 mm. The height of the web member 120 is about 0.18 mm measured at its maximum. The width of the web member 120 is about 0.11 mm measured at the mid-line. The angle $A_o$ of the flange is about 14 degrees.

A test was performed in which the force needed to bend the needle 10 was measured. This was compared to a needle of 0.46 mm in diameter which was shaped to a rectangle having a thickness of 0.37 mm and a height of 0.42 mm. The needle 10 showed a 41% increase in the force necessary to bend it as compared to the rectangular needle.

EXAMPLE 2

The needle 10 of Example 1 is used to suture a wound in mammalian tissue by initially grasping the elongated member 20 at its center with a conventional needle holder. The suture is a size 5/0 Ethibond TM silk or Prolene TM suture manufactured by Ethicon, Inc., Somerville, N.J. The point 50 is the inserted into the tissue on one side of the wound and pushed into the tissue until the point 50 exits from the tissue on the other side of the wound. The needle 10 is released from the needle holder and is then grasped proximal to the point 50 with the needle holder and pulled out of the tissue so that a section of suture remains in the tissue within the pathway created by the needle. The needle 10 does not bend or buckle when inserted into the tissue and has a resistance to penetration similar to conventional surgical needles having conventional configurations. The elongated member 20 is easily held by the needle holder and does not twist while in the needle holder.

Although this invention has been shown and described with respect to detailed embodiments thereof, it will be understood by those skilled in the art that various changes in form and detail thereof may be made without departing from the spirit and scope of the claimed invention.

What is claimed is:

1. A surgical needle comprising:

an elongated member having a proximal end and a distal end;

a piercing point extending from the distal end of the elongated member; and, a cylindrical mounting section extending from the proximal end of the elongated member and containing a cavity therein for receiving the end of a suture, wherein the elongated member has an I-beam cross-section comprising two opposed flange members connected by a web member.

2. The needle of claim 1 comprising a curved member.

3. The needle of claim 1 comprising a straight member.

4. The needle of claim 1 wherein the point comprises a blunt tip.

5. The needle of claim 1 wherein the point comprises a cutting tip.

6. The needle of claim 1 wherein at least one dimension of the I-beam cross-section varies from a maximum to a minimum adjacent to the piercing point.

7. The needle of claim 1 wherein at least one dimension of the I-beam cross-section varies from a maximum to a minimum adjacent to the cylindrical mounting section.

8. The combination comprising a surgical needle and a surgical suture, wherein the needle comprises:

an elongated member having a proximal end and a distal end;

a piercing point extending from the distal end of the elongated member; and, a cylindrical mounting section extending from the proximal end of the elongated member and containing a cavity therein for receiving the end of a suture, wherein the elongated member has an I-beam cross-section comprising two opposed flange members connected by a web member.

9. The needle of claim 8 comprising a curved member.

10. The needle of claim 8 comprising a straight member.

11. The needle of claim 8 wherein the point comprises a blunt tip.

12. The needle of claim 8 wherein the point comprises a cutting tip.

13. The needle of claim 8 wherein at least one dimension of the I-beam varies from a maximum to a minimum area adjacent to the piercing point.

14. The needle of claim 8 wherein at least one dimension of the I-beam cross-section varies from a maximum to a minimum adjacent to the cylindrical mounting section.

15. A method of suturing mammalian tissue with a surgical needle and suture, comprising inserting a surgical needle having an I-beam cross-section into tissue surrounding the wound and creating at least one needle pathway in the tissue; and, moving the suture through each needle pathway, wherein the needle comprises, an elongated member having a proximal end and a distal end;

a piercing point extending from the distal end of the elongated member; and, a cylindrical mounting section extending from the proximal end of the elongated member and containing a cavity therein for receiving the end of a suture, wherein the elongated member has an I-beam cross-section comprising two opposed flange members connected by a web member.

16. The method of claim 15 wherein the needle comprises a curved member.

17. The method of claim 15 wherein the needle comprises a straight member.

18. The method of claim 15 wherein the point of the needle comprises a blunt tip.

19. The method of claim 15 wherein the point of the needle comprises a cutting tip.

20. The needle of claim 15 wherein at least one dimension of the I-beam cross-section tapers from a maximum to a minimum adjacent to the piercing point.

21. The needle of claim 15 wherein a least one dimension of the I-beam cross-section tapers from a maximum area to a minimum adjacent to the cylindrical mounting section.

* * * * *